US012751932B2

(12) United States Patent
Laval et al.

(10) Patent No.: US 12,751,932 B2
(45) Date of Patent: Oct. 6, 2026

(54) COMPOSITIONS COMPRISING CURCUMINOIDS FOR USE IN THE TREATMENT OF MUSCLE SORENESS

(71) Applicant: Givaudan SA, Vernier (CH)

(72) Inventors: Julie Laval, Avignon (FR); Pascale Elizabeth Reneé Fança-Berthon, Le Thor (FR); Sandra Naranjo Modad, Avignon (FR)

(73) Assignee: GIVAUDAN SA, Vernier (CH)

(*) Notice: Subject to any disclaimer, the term of this patent is extended or adjusted under 35 U.S.C. 154(b) by 214 days.

(21) Appl. No.: 18/569,901

(22) PCT Filed: Jun. 15, 2022

(86) PCT No.: PCT/EP2022/066392

§ 371 (c)(1), (2) Date: Dec. 13, 2023

(87) PCT Pub. No.: WO2022/263558

PCT Pub. Date: Dec. 22, 2022

(65) Prior Publication Data

US 2025/0127731 A1 Apr. 24, 2025

(30) Foreign Application Priority Data

Jun. 15, 2021 (GB) ..................................... 2108511

(51) Int. Cl.

| | |
|---|---|
| ***A61K 36/00*** | (2006.01) |
| ***A61K 9/00*** | (2006.01) |
| ***A61K 31/12*** | (2006.01) |
| ***A61K 36/185*** | (2006.01) |
| ***A61K 36/9066*** | (2006.01) |
| ***A61K 47/36*** | (2006.01) |
| ***A61P 21/06*** | (2006.01) |
| ***A61P 29/00*** | (2006.01) |

(52) U.S. Cl.

CPC ............ *A61K 31/12* (2013.01); *A61K 9/0056* (2013.01); *A61K 36/185* (2013.01); *A61K 36/9066* (2013.01); *A61K 47/36* (2013.01); *A61P 21/06* (2018.01); *A61P 29/00* (2018.01)

(58) Field of Classification Search

CPC .................................................. A61K 36/9066

See application file for complete search history.

(56) References Cited

U.S. PATENT DOCUMENTS

| | | | |
|---|---|---|---|
| 2009/0304602 | A1 | 12/2009 | Tuchinsky |
| 2015/0297536 | A1 | 10/2015 | Deshpande et al. |

FOREIGN PATENT DOCUMENTS

| | | | | |
|---|---|---|---|---|
| CN | 106579392 A | 4/2017 | | |
| CN | 106616980 A | 2/2021 | | |
| WO | WO-2020030611 A1 * | 2/2020 | ............. | A61Q 19/00 |
| WO | 2021090154 A1 | 5/2021 | | |

OTHER PUBLICATIONS

Great Britain Search Report for Application No. GB2108511.3 dated Dec. 1, 2021.

International Search Report for Application No. PCT/EP2022/066392 dated Sep. 29, 2022.

International Written Opinion for Application No. PCT/EP2022/066392 dated Sep. 29, 2022.

Hanif Mughal Muhammad et al: "Turmeric polyphenols: A comprehensive review", Integrative Food, Nutrition and Metabolism, pp. 1-6, vol. 6, No. 6, dated Nov. 10, 2019.

M. Najmul Ghani Khan: "Takmeed Barae-tasekeen", Traditional Knowledge Digital Library, JA6/1040E, retrieved Jul. 4, 2023.

Z. Bara Soojan Wa Waja: "Zimaad Bara Soojan Wa Waja", Mohammad Najmul Ghani Khan, JA6/611J, retrieved Jul. 4, 2023.

M. Najmul Ghani Khan: "Nuskha Barae Wajagh-ul-Mafaasil", Traditional Knowledge Digital Library, AN2/101, retrieved Jul. 4, 2023.

M. Azam Khan: "Nuskha Bara-e Waja-e Mafaasil":, Traditional Knowledge Digital Library, BA4/320A, retrieved Jul. 4, 2023, retrieved Jul. 4, 2023.

M. Najmul Ghani Khan: "Palak Ke Beej (tukhm-e-Asfanaakh", Traditional Knowledge Digital Library, AN2/11, retrieved Jul. 4, 2023.

Anonymous: "Peedantak Vati Tablets", Database GNPD, dated Apr. 25, 2017; XP055962388, Database accession No. 4766425.

* cited by examiner

*Primary Examiner* — Qiuwen Mi

(74) *Attorney, Agent, or Firm* — Curatolo Sidoti & Trillis Co., L.P.A.; Salvatore A. Sidoti; Floyd Trillis, III

(57) ABSTRACT

The present invention relates to the use of an improved curcuminoids composition for improving and/or maintaining functional performance and/or relieving, treating, decreasing and/or preventing muscle soreness in a subject during and/or after exercise.

23 Claims, 1 Drawing Sheet

Please select the answer in each row that best describes your current state:

| | 5 | 4 | 3 | 2 | 1 | Record Score |
|---|---|---|---|---|---|---|
| **Fatigue** | Very fresh | Fresh | Normal | More tired than normal | Always tired | |
| **Sleep Quality** | Very restful | Good | Difficulty falling asleep | Restless sleep | Insomnia | |
| **General Muscle Soreness** | Feeling great | Feeling good | Normal | Increase in soreness/ tightness | Very sore | |
| **Stress Levels** | Very relaxed | Relaxed | Normal | Feeling stressed | Highly stressed | |
| **Mood** | Very positive mood | A generally good mood | Less interested in others &/or activities than usual | Snappiness at team-mates, family, and co-workers | Highly annoyed/ irritable/ down | |

COMPOSITIONS COMPRISING CURCUMINOIDS FOR USE IN THE TREATMENT OF MUSCLE SORENESS

CROSS REFERENCE TO RELATED APPLICATIONS

The present patent application is a national stage patent application of International Application No. PCT/EP2022/066392, filed 15 Jun. 2022, which claims priority from Great Britain Application No. 2108511.3, filed 15 Jun. 2021, both of which are hereby incorporated by reference.

FIELD OF THE INVENTION

The present invention relates to the use of an improved curcuminoids composition for improving and/or maintaining functional performance and/or relieving, treating, decreasing and/or preventing muscle soreness in a subject during and/or after exercise

BACKGROUND OF THE INVENTION

Turmeric is a widely used spice and also colouring/flavouring substance that comes from the root of Turmeric plant (*Curcuma longa*). It has been used for centuries in traditional medicine in Asian countries and has been shown to improve numerous health conditions.

Turmeric is on the GRAS (generally recognised as safe) substance list of the US Food and Drugs Administration (FDA).

Turmeric was found to be effective even when given by different routes, including topical, oral or by inhalation, dependent on the intended use. The major constituent of turmeric is curcumin (diferuloylmethane), which constitutes up to 70-85% of the total curcuminoid content, with demethoxycurcumin and bis-demethoxycurcumin comprising the remainder (Aggarwal, B. B., & Shishodia, S. (2004). *Annals of the New York Academy of Sciences,* 1030, 434-441). Curcumin and curcuminoids have been extensively investigated due to their antioxidant and anti-inflammatory properties, notably regarding their potential efficacy in modulating various health conditions (Hewlings, S., & Kalman, D. (2017). Curcumin: A Review of Its' Effects on Human Health. *Foods,* 6(10), 92). While the molecular structure of curcumin and curcuminoids is responsible for their free radical scavenging activity, protective effect of curcumin has been also strongly associated to the combination of Nrf-2 activation and NFkappaB inhibition (Aggarwal & Harikumar, 2009; Williams, Sorribas, & Howes, 2011). Curcumin modulation of these two cellular pathways is respectively involved into the induction of ARE genes (antioxidant response elements, notably regulating the expression of HO-1, GSH synthesis enzymes, SOD, catalase), and the reduction of cyclooxygenase-2 activity (COX-2) and pro-inflammatory cytokine production (e.g., TNFalpha, IL1beta, IL6) (Menon, V. P., & Sudheer, A. R. (2007). *Advances in Experimental Medicine and Biology*, Vol. 595, pp. 105-125; Esatbeyoglu, T. et al. (2012, May 29). *Angewandte Chemie—International Edition*, Vol. 51, pp. 5308-5332.). Pre-clinical studies in mice showed several benefits of curcumin and curcuminoids after downhill exercise, such as muscle regeneration, improved behaviours associated with delayed onset muscle soreness (DOMS) with extended voluntary running, decreased level of IL-6, TNFalpha, CK and oxidative stress induced by hydrogen peroxide (Kawanishi, N., et al. (2013). *Biochemical and Biophysical Research*

*Communications,* 441(3), 573-578; Davis, J. M., et al. (2007). *American Journal of Physiology—Regulatory Integrative and Comparative Physiology,* 292(6).). While during these studies, turmeric food was given orally to animals, Thaloor and colleagues treated mice intra-peritoneal with curcumin, and could restore normal muscle architecture after local freeze injury (Thaloor, D., et al. (1999). *American Journal of Physiology—Cell Physiology,* 277(2 46-2).). All these results indicate that curcumin and curcuminoids, through their physiological effects on inflammation and oxidative stress, can have a positive effect on exercise-induced muscle damage (EIMD) and associated-muscle injuries.

Turmeric (*Curcuma longa* L.) extracts have a long history of use worldwide with a good safety profile. However, very high doses of turmeric standard extracts (up to 6000 mg) or enhanced formulation (600 to 2500 mg) are needed to be administrating to have an effect in muscle recovery and muscle function after exercise.

For example, 2000 mg of formulation containing 400 mg of curcuminoids were used in the clinical study of Drobnic F. Et al (Journal of the international society of sport nutrition. 2014. 11:31). Other studies using also high levels of curcuminoids did not shown any significant results of the reduction of muscles soreness (Nicol et al., European Journal of Applied Physiology, 2015, 115 (8): 1769-77; or Jager R. et al, Nutrients 2019 Jul. 23 11(7)) where 200-1060 mg of curcuminoids where used.

SUMMARY OF THE INVENTION

The inventors have surprisingly found that a specific composition comprising curcuminoids, acacia gum and *quillaja* have an improved effect on muscle soreness and functional muscle performance for example after exercise or intense exercise.

The composition of the invention differs from the standard turmeric extract, and allows a positive effect on muscle soreness and functional muscle performance even using a significant lower dosage of the active compounds.

Very high doses of turmeric standard extracts (up to 6000 mg) or enhanced formulation (600 to 2500 mg) are needed to be administrating to have an effect in muscle recovery and muscle function after exercise.

A similar or even improved effect on muscle soreness, functional muscle performance, perceived wellness and wellbeing and perceived exertion is shown with the composition of the invention at much lower curcuminoids doses. The composition of the invention reduces muscle soreness and improves functional muscle performance in subjects after exercise even at a daily dose of only 90 mg of curcuminoids.

This is a 10 to 20 time reduction of the active daily dose of curcuminoids.

The reduction of the effective daily dose has the additional advantage that the administration format is reduced (i.e smaller pills can be produced) with the same efficacy. Another advantage is that the administration of the active compounds (curcuminoids) may be also presented as a single dosage in a one daily dose. The presentation in smaller doses of the compositions of the invention with the possibility of one single daily dose of the active compounds will have a positive effect in the management of muscle soreness and functional muscle performance after exercise.

Accordingly, in a first aspect, the invention provides a composition comprising i) curcumi-noids; ii) modified starch and/or acacia gum; and iii) one or more saponins (such as *quillaja*), for use in improving and/or maintaining functional performance and/or relieving, treating, decreasing and/or preventing muscle soreness in a subject, wherein the composition comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

In a second aspect, the invention provides the use of a composition comprising i) curcuminoids; ii) modified starch and/or acacia gum; and iii) one or more saponins (such as *quillaja*) for improving and/or maintaining functional performance and/or relieving, treating, decreasing and/or preventing muscle soreness in a subject, wherein the composition comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

In a third aspect, the invention provides a method for improving and/or maintaining functional performance and/or relieving, treating, decreasing and/or preventing muscle soreness in a subject comprising the administration of an effective amount of a composition comprising i) curcuminoids; ii) modified starch and/or acacia gum; and iii) one or more saponins (such as *quillaja* saponins) to a subject in need thereof and wherein the composition comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

The decrease in functional performance and/or muscle soreness may be caused by one or more of the following conditions: an exercise (such as an intense exercise), a traumatic injury, muscle inflammation, Inflammatory myopathies etc.

In a preferred embodiment, decrease in functional performance and/or the muscle soreness is caused by exercise such as intense exercise.

Accordingly, the invention provides a composition comprising i) curcuminoids; ii) modified starch and/or acacia gum; and iii) one or more saponins (such as *quillaja*), for use in improving and/or maintaining functional performance and/or relieving, treating, decreasing and/or preventing muscle soreness in a subject during and/or after exercise, wherein the composition comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/doses.

Accordingly, the invention provides the use of a composition comprising i) curcuminoids; ii) modified starch and/or acacia gum; and iii) one or more saponins (such as *quillaja*) for improving and/or maintaining functional performance and/or relieving, treating, decreasing and/or preventing muscle soreness in a subject during and/or after exercise, wherein the composition comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

Accordingly, the invention provides a method for improving and/or maintaining functional performance and/or relieving, treating, decreasing and/or preventing muscle soreness in a subject during and/or after exercise comprising the administration of an effective amount of a composition comprising i) curcuminoids; ii) modified starch and/or acacia gum; and iii) one or more saponins (such as *quillaja* saponins) to a subject in need thereof and wherein the composition comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

The details, examples and preferences provided in relation to any one or more of the stated aspects of the present invention will be further described herein and apply equally to all aspects of the present invention. Any combination of the embodiments, examples and preferences described herein below in all possible variations thereof is encompassed by the present invention unless otherwise indicated herein, or otherwise clearly contradicted by context.

DETAILED DESCRIPTION OF THE INVENTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, etc are hereby expressly incorporated by reference for the portions of the document discussed herein, as well as in their entirety.

According to the present invention, there is provided a composition comprising i) curcumi-noids; ii) modified starch and/or acacia gum; and iii) one or more saponins (such as *quillaja*), for use in improving and/or maintaining functional performance and/or relieving, treating, decreasing and/or preventing muscle soreness in a subject, wherein the composition comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

Such compositions maybe referred to hereinafter as the "composition for use of the invention" or "composition of the invention".

The decrease in functional performance and/or muscle soreness may be caused by one or more of the following conditions: an exercise (such as an intense exercise), a traumatic injury, muscle inflammation, Inflammatory myopathies etc.

In a preferred embodiment, decrease in functional performance and/or the muscle soreness is caused by exercise such as intense exercise.

Accordingly, the invention provides a composition comprising i) curcuminoids; ii) modified starch and/or acacia gum; and iii) one or more saponins (such as *quillaja*), for use in improv-ing and/or maintaining functional performance and/or relieving, treating, decreasing and/or preventing muscle soreness in a subject during and/or after exercise, wherein the compo-sition comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/doses.

The present invention, also provides the use of a composition comprising i) curcuminoids; ii) modified starch and/or acacia gum; and iii) one or more saponins (such as *quillaja* saponins) for improving and/or maintaining functional performance and/or relieving, treating, decreasing and/or preventing muscle soreness in a subject, wherein the composition comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

Such use maybe referred to hereinafter as the "use of the invention".

The decrease in functional performance and/or muscle soreness may be caused by one or more of the following conditions: an exercise (such as an intense exercise), a traumatic injury, muscle inflammation, Inflammatory myopathies etc.

In a preferred embodiment, decrease in functional performance and/or the muscle soreness is caused by exercise such as intense exercise.

Accordingly, the invention provides the use of a composition comprising i) curcuminoids; ii) modified starch and/or acacia gum; and iii) one or more saponins (such as *quillaja*) for im-proving and/or maintaining functional performance and/or relieving, treating, decreasing and/or preventing muscle soreness in a subject during and/or after exercise, wherein the composi-tion comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

According to the present invention, there is also provided a method for improving and/or maintaining functional performance and/or relieving, treating, decreasing and/or preventing muscle soreness in a subject during and/or after exercise comprising the administration of an effective amount of a composition comprising i) curcuminoids; ii) modified starch and/or acacia gum; and iii) one or more saponins (such as *quillaja* saponins) to a subject in need thereof and wherein the composition comprising curcuminoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

Such method maybe referred to hereinafter as the "method of the invention".

According to the present invention, in the composition for use, methods or uses described herein, the muscle soreness may be delayed onset muscle soreness and/or acute muscle soreness. In a preferred embodiment, the muscle soreness is exercise-induced muscle soreness.

In the present invention "Delayed onset muscle soreness (DOMS)" may refer to the pain and stiffness felt in muscles several hours to days after unaccustomed or strenuous exercise.

The soreness is felt most strongly 24 to 72 hours after the exercise. It is thought to be caused by eccentric (lengthening) exercise, which causes small-scale damage (microtrauma) to the muscle fibers.

Delayed onset muscle soreness is one symptom of exercise-induced muscle damage. The other is acute muscle soreness, which appears during and immediately after exercise.

In the present invention "Acute muscle soreness (AMS)" may refer to the pain felt in muscles during and immediately, up to 24 hours, after strenuous physical exercise. The pain appears within a minute of contracting the muscle and it will disappear within two or three minutes or up to several hours after relaxing it.

The following causes have been proposed for acute muscle soreness: Accumulation of chemical end products of exercise in muscle cells such as lactic acid and H+ or muscle fatigue (the muscle tires and cannot contract any more).

In one embodiment of the composition, use or method of the invention the improving and/or maintaining functional performance is due by one or more of: improving and/or maintaining muscle recovery, improving and/or maintaining muscle function, improving and/or maintaining muscle power, improving and/or maintaining muscle strength or improving and/or maintaining perceived wellness and wellbeing or improving and/or maintaining perceived exertion.

In the present invention, "muscle power" may be defined as the amount of work performed per unit of time. The ability to exert a maximal force in as short a time as possible, as in accelerating, jumping and throwing implements. While in the present invention, "muscle strength" may be defined as the maximal force you can apply against a load, power is proportional to the speed at which you can apply this maximal force. Methods for assessing muscle power and strength are well known in the art such as the methods used in the examples of the present description (measuring vertical jump tests recording height, velocity and power)

In the present invention, "perceived wellness and wellbeing" may refer to fatigue, sleep quality, general muscle soreness, stress, and mood individually or in composite.

In the present invention, "perceived exertion" may refer to difficulty of breathing and exhaustion.

In one embodiment, the muscle function is isometric and/or isokinetic muscular function.

In one embodiment, the improvement on functional performance (i.e the improvement of muscle recovery, improvement of muscle function, improvement of muscle power, improvement of muscle strength and/or improvement of perceived wellness and wellbeing) is during the exercise or on the first 24 hours after the exercise.

In another embodiment, the improvement on functional performance (i.e the improvement of muscle recovery, improvement of muscle function, improvement of muscle power, improvement of muscle strength and/or improvement of perceived wellness and wellbeing) is perceived after 24 hours after the exercise, such as 24 to 72 hours after the exercise, such as after 48 hours or more.

In one embodiment, relieve, treatment, decrease and/or prevention of muscle soreness is perceived during the exercise or on the first 24 hours after the exercise and longer.

In another embodiment, relieve, treatment, decrease and/or prevention of muscle soreness is perceived after 24 hours after the exercise, such as 24 to 72 hours after the exercise, such as after 48 hours or more.

In one embodiment the subject is a healthy subject.

The invention is also related to a composition comprising i) curcuminoids; ii) modified starch and/or acacia gum; and iii) one or more saponins for use in decreasing the levels of creatine kinase (CK) in a subject during and/or after exercise or in preventing the increase of the levels of creatine kinase (CK) in a subject during and/or after exercise, wherein the composition comprising curcu-minoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

The invention is also related to the use of a composition comprising i) curcuminoids; ii) modified starch and/or acacia gum; and iii) one or more saponins for use in decreasing the levels of creatine kinase (CK) in a subject during and/or after exercise or in preventing the increase of the levels of creatine kinase (CK) in a subject during and/or after exercise, wherein the composition comprising curcu-minoids may be administered or used to provide curcuminoids in an amount of from about 50 mg/dose to about 300 mg/dose, such as about 60 mg/dose, 70 mg/dose, 80 mg/dose, 90 mg/dose, 100 mg/dose, 150 mg/dose, 200 mg/dose or 300 mg/dose.

The invention is also related to a method for use in decreasing the levels of creatine kinase (CK) in a subject during and/or after exercise or in preventing the increase of the levels of creatine kinase (CK) in a subject during and/or after exercise, comprising the administration of an effective amount of a composition comprising i) curcuminoids; ii) modified starch and/or acacia gum; and iii) one or more saponins to a subject in need thereof, wherein the composition comprising curcuminoids may be admin-istered or used to provide curcuminoids in an amount of from about 50 mg/dose to about 300 mg/dose, such as, about 60 mg/dose, 70 mg/dose, 80 mg/dose, 90 mg/dose, 100 mg/dose, 150 mg/dose, 200 mg/dose or 300 mg/dose.

The invention is also related to a composition comprising i) curcuminoids; ii) modified starch and/or acacia gum; and iii) one or more saponin(s) for the manufacture of a medicament for use in decreasing the levels of creatine kinase (CK) in a subject during and/or after exercise or in preventing the increase of the levels of creatine kinase (CK) in a subject during and/or after exercise in a subject by oral administration.

Creatine kinase (CK) is a well-known biomarker of damage in muscles (such as skeletal muscles). The levels of CK may be measured in the blood using techniques well known in the art. The inventors of the present application have demonstrated that the compositions of the invention prevent and decreases the formation of CK during exercise.

The composition of the "composition for use of the invention", of the "use of the invention" and of the "method of the invention" may be in the form of a colloidal suspension or an emulsion or may be in the form a solid, for example, in the form of a powder.

As used herein, the term "emulsion" refers to a type of colloid that is formed by combining two liquids that do not usually mix. Typically, one of the liquids will contain a dispersion of the other liquid.

Sometimes the terms "colloid" and "emulsion" are used interchangeably, but as used herein the term emulsion applies when both phases of a mixture are liquids. The particles in a colloid can be any phase of matter. So, an emulsion is a type of colloid, but not all colloids are emulsions. In certain embodiments, the compositions of the invention form a colloidal solution, occasionally identified as a colloidal suspension, this is a mixture in which the substances (such as solids, like the curcuminoids) are regularly suspended in a fluid.

Some compositions of the invention do not comprise fenugreek, for example, some compositions of the invention do not comprise fenugreek fibre (i.e. fibre obtained or obtainable from fenugreek).

The composition of the invention may comprise small amounts of polyols and/or low molecular weight sugars with preferably 1 or 2 monosaccharide units, such as less than 5% by weight of the composition or less than 2.5% by weight of the composition. Alternatively, the composition of the invention may be free of polyols and/or low molecular weight sugars such as those with 1 or 2 monosaccharide units, i.e. some compositions do not contain any polyols and/or low molecular weight sugars, such as those with 1 or 2 monosaccharide units.

In the composition of the invention, the particles may have an average diameter of from about 200 nm, 300 nm, 400 nm, 500 nm, 600 nm, 700 nm, 800 nm, 900 nm, 1000 nm, 1100 nm, 1200 nm, 1300 nm, 1400 nm or 1500 nm to about 9000 nm, 8000 nm, 7000 nm, 6000 nm, 5000 nm, 4000 nm, 3000 nm or 2000 nm, such as from about 1000 nm to about 6000 nm. The particles may also have an average diameter of from about 200 nm to about 600 nm, or from about 300 nm to about 500 nm or about 400 nm.

For example, where the composition is in the form of an emulsion or a coloid, the composition may, for example, comprise particles having an average diameter of from about 550 nm to about 700 nm and particles having an average diameter of from about 100 nm to about 250 nm giving an average diameter of about 400 nm.

Where the composition is in the form of a solid, such as a powder, the composition may, for example, comprise particles having an average diameter of from about 1000 nm to about 6000 nm, such as from about 2000 nm to about 4000 nm.

The particles in the composition of the invention may be in the form of micelles.

In the composition of the invention, for example where the composition is in the form of a solid, the particles may be formed using such techniques known in the art, such as spray drying.

After the formation of the particles (for example, after drying, such as spray drying) the particles may be ground and/or milled (such as ball milled) to provide a more uniform size.

The size and morphology of loaded curcumin micelle were analyzed by dynamic light scattering (DLS), and zeta potential (Z-potential), and scanning electron microscopy (SEM). For DLS and zeta-potential analyses a Zetasizer Nano ZS (NanoZS90, Malvern Instrument Ltd., UK) with a He/Ne laser ($\lambda$=633 nm) at a fixed scattering angle of 90° at temperature of (25±0.1° C.). For example, the size of the particles may be measured by method CQ-MO-304.

In the composition of the invention, the curcuminoids may be obtained from any source. However, it is preferred that the curcuminoids are obtained from a natural source, i.e. the curcuminoids are not synthetic, but are plant based.

In the methods or uses described herein, the curcuminoids may be selected from the group consisting of curcumin and its phase I or phase II metabolites, demethoxycurcumin and its phase I or phase II metabolites, bisdemethoxycurcumin and its phase I or phase II metabolites and mixtures thereof. For example, the phase I and/or phase II metabolites may be selected from the group consisting of curcumin glucuronide, curcumin sulfate, DMC glucuronide, DMC sulfate, BDMC glucuronide, BDMC sulfate, tetra-hydrocurcumin (THC), THC glucuronide, THC sulfate, hexahydrocurcumin (HHC), HHC glucuronide, HHC sulfate and mixtures thereof.

In the compositions for use, methods or uses described herein, the curcuminoids may be in their unmetabolized form (i.e. free form), for example the forms or curcumin, DMC and BDMC that have not undergone glucuronide or sulfate addition.

The composition of the invention may comprise at least about 10%, at least about 25% curcuminoids, at least about 30%, at least about 40%, at least about 50%, at least about 60%, at least about 70%, at least about 80%, at least about 90%, at least about 95%, at least about 99% curcuminoids by weight of the composition.

For example, in the methods or uses described herein, in the composition the curcuminoids may be present in an amount from about 20% to about 60%, such as from about 25% to about 50%, or from about 28% to about 48% by weight of the composition.

For example, in the methods or uses described herein in the composition of the invention the curcuminoids may be present in an amount from about 30 mg, 40 mg, 45 mg, 50 mg, 55 mg, 60 mg, 65 mg, 70 mg, 75 mg, 80 mg, 85 mg or 90 mg to about 1500 mg, 1400 mg, 1200 mg, 1100 mg, 1000 mg, 900 mg, 800 mg, 700 mg, 600 mg, 500 mg, 400 mg, 300 mg, 250 mg, 200 mg, 150 mg, 100 mg or 95 mg, such as from about 70 mg to about 300 mg, or from about 70 mg to about 200 mg, or from about 70 mg to about 100 mg, such as 90 mg.

The curcuminoids may be provided by extraction and optionally purification from the root (rhizome) of turmeric (*Curcuma longa*), oleoresin turmeric root, defatted oleoresin turmeric root and mixtures thereof, i.e. the curcuminoids may be in the form of an extract or purified extract of turmeric comprising from about 30% to about 100% curcuminoids, such as from about 35%, 40%, 45%, 50%, 55%, 60%, 65%, 70%, 75%, 80%, 85% or 90% to about 95%, 90%, 85%, 80%, 75%, 70%, 65%, 60%, 55%, 50% or 45% curcuminoids based on the percentage of total curcuminoids in the extract.

Where the curcuminoids are provided as an extract of turmeric, the turmeric may be extracted using an alcohol-based extraction solvent, such as a water/alcohol mixture or an alcohol, an organic based extraction solvent or any other technique and solvent that allows having high yields of curcuminoids. For example, the alcohol-based extraction solvent may be water/methanol (i.e. a mixture of water and methanol) or water/ethanol (i.e. a mixture of water and ethanol) or methanol or ethanol.

Where the extraction solvent comprises a water/alcohol mixture the ratio of water to alcohol may be from about 25:75 to about 1:99, such as from about 20:80 to about 5:95 or about 10:90. For example, the ex-traction solvent may be water/ethanol in a ratio of from about 25:75 to about 1:99, such as from about 20:80 to about 5:95 or about 10:90 The turmeric extract may then be further purified to provide an extract of curcuminoids comprising from about 30% to about 100% curcuminoids, such as from about 35%, 40%, 45%, 50%, 55%, 60%, 65%, 70%, 75%, 80%, 85% or 90% to about 95%, 90%, 85%, 80%, 75%, 70%, 65%, 60%, 55%, 50% or 45% curcuminoids based on the percentage of total curcuminoids in the extract.

The purification of the extract may be performed using such techniques known in the art. Typically, the extract is purified using an alcohol-based solvent, such as 100% methanol or 100% ethanol.

The turmeric extract may optionally be dried to remove any excess solvent.

Where the curcuminoids are provided in the form of a turmeric extract as previously defined, the composition may comprise from about from about 30% to about 80% turmeric extract, such as from about 35% to about 45% by weight of the composition. For example, the composition may comprise from about 35% (i.e. 35%) to about 45% turmeric extract by weight of the composition, where the turmeric extract comprises from about 85% to about 95% curcuminoids by weight of the turmeric extract, providing a composition that comprises from about 30% (i.e. 30%) to about 43% curcuminoids by weight of the composition.

The curcuminoids may be provided as a liquid or a powder, such as a powder. For example, a powdered turmeric extract.

As used herein, the term "curcuminoids" includes curcumin, demethoxycurcumin (DMC), and bisdemethoxycurcumin (BDMC). For example, the turmeric extract may comprise from about 70% to about 85% curcumin (such as from about 75% to about 80%), from about 10% to about 25% DMC (such as from about 15% to about 20%) and from about 0% to about 10% BDMC. For example the composition may comprise from about 60 mg to about 90 mg of curcuminoids, with from about 54 mg to about 69 mg curcumin and from 6 mg to about 11 mg of DMC and BDMC. In a preferred embodiment, the composition may be administered or used to provide curcuminoids in an amount of from about 70, 80, 90, 95, 100, 150, 200, 250 mg/day to about 1500, 1400, 1300, 1200, 1100, 1000, 900, 850, 800, 750, 700, 650, 600, 550, 500, 450, 400, 350, 300 mg/day of curcuminoids, such as from about 70 mg/day to about 150 mg/day of curcuminoids, such as from about 70 mg/day to about 90 mg/day of curcuminoids. In an embodiment the ratio between curcumin and DMC/BDMC is from 7:3 to 8:2. In a preferred embodiment, the curcumin provided is from about 54 mg/day to about 69 mg/day and the DMC and BDMC is from 16 mg/day to about 21 mg/day.

In the methods or uses described herein, the acacia gum (or Arabic gum) in the composition may be present in an amount from about 30%, 35%, 40%, 45%, 50%, 55%, to about 85%, 80%, 75%, 70%, 65%, 60% by weight of the composition, such as from about 50% to about 60% by weight of the composition or about 58% by weight of the composition.

In the methods or uses described herein, the modified starch in the composition may be present in an amount from about 40% to about 65% by weight of the composition, such as from about 50 to about 60% by weight of the composition or about 58% by weight of the composition.

Saponins are a group of naturally occurring glycosides, predominantly found in the plant kingdom. They comprise a non-carbohydrate aglycone coupled to sugar chain units. Sap-onins are divided in two groups: steroidal and triterpene saponins. Over 100 steroidal and an even higher number of triterpene saponins have been so far identified. (K. Hostettmann, & A. Marston, Saponins (Cambridge University Press 1995). As used herein, the term "saponin(s)" includes one or more saponins from natural (such as *quillaja* or *yucca* saponins) or synthetic origin as well as an extract obtained or obtainable from any vegetal, animal or bacterial source of saponin, for example *quillaja, yucca* etc. The saponin of the present invention can be of natural origin or of synthetic origin. It may be one or more saponins from the same or different origin.

For example, the saponin(s) can be obtained or obtainable from plants such as soya, beans, peas, *Solanum* and *Allium* species, tomato, asparagus, tea, peanut, spinach, sugar beet, yam, blackberry, liquorice root, primula root, senega root, tea, ginseng, *Quillaja* (such as *Quillaja saponaria*), *Yucca* (such as *Yucca shidigera*), and/or Gyposphila. In one embodiment the one or more saponins is *quillaja* saponin(s). In one preferred embodiment, the saponin is not a ginger saponin.

The one or more saponins used in the present invention can be highly purified or may be a natural extract with different concentrations of saponins.

In certain embodiments, the one or more saponin(s) is selected from purified *quillaja* saponin(s) from natural or synthetic origin or an extract obtained or obtainable from *quillaja* and mixtures thereof.

As used herein, the term "*quillaja* saponin(s)", "*yucca* saponi(s)", etc, means one or more saponins that can be obtained or obtainable from any of the members of the *quillaja* family, or the *yucca* family or any of the plants that contains saponins such as the ones described before. The *quillaja* saponin or the mixture of *quillaja* saponins (or the *yucca* saponin or the mixture of *yucca* saponins) can be of synthetic or natural origin.

As will be appreciated by the person skilled in the art, as used herein the term "obtainable from" means that the saponin(s) may be obtained from a plant or may be isolated from the plant, or may be obtained from an alternative source, for example by chemical synthesis or enzymatic production. Whereas the term "obtained" as used herein, means that the sapo-nin(s) is directly derived from the plant. For example in one embodiment, the saponin(s) can be a "natural extract comprising saponin(s)".

The at least one saponin, may be of natural or synthetic origin.

A "purified saponin(s)" means one or more saponins of natural or synthetic origin that have a concentration of at least about 80%, at least about 90%, at least about 95%, at least about 99%, at least about 99.9% of one or more saponins as described before (such as *quillaja* saponin(s) and/or *yucca* saponin(s)).

A "saponin(s) comprising extract" means any natural extract comprising at least one type of saponin as described before that may be derived from, e.g., but not limited to soya, beans, peas, oat, *Solanum* and *Allium* species, tomato, asparagus, tea, peanut, spinach, sugar beet, yam, blackberry, liquorice root, primula root, senega root, *Quillaja* (such as *Quillaja saponaria*), *Yucca* (such as *Yucca shidigera*), and/or Gyposphila.

According to the present invention, the at least one saponin may be derived from a single source or from multiple sources.

According to the present invention, the at least one saponin comprising extract may be derived from a single source or from multiple sources.

In one embodiment the saponin component is a natural extract, such as a *quillaja* extract, tea extract, licorice extract, beet root extract, sugar beet extract, ginseng extract, oat extract, *yucca* extract or a mixture thereof, with at least 5% wt/wt, or at least 10% wt/wt, or at least 15% wt/wt, or at least 20% wt/wt, or at least 25% wt/wt, or at least 30% wt/wt, or at least 35% wt/wt, or at least 40% wt/wt, or at least 50% wt/wt, or at least 60% wt/wt, or at least 70% wt/wt, or at least 80% wt/wt of saponins. In one embodiment the saponin component may be a *quillaja* extract with at least 60% saponins, such as 65% wt/wt of saponins.

In a preferred embodiment, the saponin(s) is *quillaja*. As used herein, the term "*quillaja*" includes one or more purified *quillaja* saponins from natural or synthetic origin as well as an extract obtained or obtainable from *quillaja*.

The saponin(s) (such as *quillaja* saponins) of the composition of the invention may be present in an amount from about 0.1%, 0.2%, 0.3%, 0.4%, 0.5%, 0.6%, 0.7%, 0.8%, 1%, 1.2%, 1.3%, 1.4%, 1.5%, 1.6%, 1.7%, 1.8%, 1.8%, 2%, 2.5%, 3%, 3.5%, 4% or 4.5% to about 5%, 4.5%, 4%, 3.5%, 3%, 2.5%, 2.4%, 2.3%, 2.2%, 2%, 1.5%, 1%, 0.8%, 0.6%, 0.5%, or to 0.2% by weight of the composition, such as from about 0.4% to about 3%, such as from 0.5% to about 2.5% or about 0.65% or about 2% by weight of the composition. In a preferred embodiment, the one or more saponin(s) are one or more *quillaja* saponin(s). In one embodiment, the *quillaja* saponins are purified *quillaja* saponins. In a more preferred embodiment, the one or more saponins may be provided as an extract obtained or obtainable from *quillaja*.

In the present invention "purified *quillaja* saponins" may refer to one of more *quillaja* saponins from natural or synthetic origin that have a purity of at least 80%, such as at least 90%, such as at least 95%, such as at least 99%.

The saponin(s) (such as a purified *quillaja* saponin(s) or such as *quillaja* extracts from or obtainable from *quillaja* containing saponin(s)) used in the process of the invention may be in any form, such as a liquid or a solid. For example, the saponin(s) may be used in the form of a solid, such as a powder.

The *quillaja* saponin(s) (such as a purified *quillaja* saponins or the extract obtained from or obtainable from *quillaja* containing saponin(s)) used in the process of the invention may be in any form, such as a liquid or a solid. For example, the *quillaja* extract may be used in the form of a solid, such as a powder.

When present in the composition of the invention, the saponin(s) (such as *quillaja* saponins) water and/or other solvent, such as alcohol, may be added to the solid or liquid saponin(s) (such as *quillaja*).

In a preferred embodiment, the one or more saponins are *quillaja* saponin(s) and are present in the final composition from about 0.5% to about 5%, such as about 0.8 to about 2%, such as from about 1% to 1.5% such as about 1.3% wt/wt.

In the methods or uses described herein, the composition may optionally comprise a plant and/or vegetable oil. For example, the composition of the invention may comprise plant and/or vegetable oils selected from the group consisting of coconut oil, corn oil, cottonseed oil, olive oil, palm oil, peanut oil (ground nut oil), rapeseed oil, including canola oil, safflower oil, sesame oil, soybean oil, sunflower oil, and mixtures thereof.

The plant and/or vegetable oil present in the composition of the invention may be present in an amount of from about 1% to about 20% plant and/or vegetable oil, such as from about 2.5% to about 10% or about 5% by weight of the composition.

In a preferred embodiment of the compositions for use, methods or uses described herein, the composition has from about 30 to about 40% of *Curcuma longa* rhizome ethanol extract (with at least 80%, such as at least 90% of curcuminoids), from about 55 to about 65% acacia gum, from about 3 to about 7%, sunflower oil and from about 1 to about 3% *quillaja* extract.

Unless otherwise stated herein, the weight percentages listed are based on the total weight of (dry) composition obtained.

According to the present invention, in the methods or uses described herein the composition comprising curcuminoids may be provided in the form of a (suitable) composition, such as a "pharmaceutical composition" or a "food composition".

In particular embodiments, the composition comprising curcuminoids may be provided in the form of a pharmaceutical composition (which may also be referred to as a pharmaceutical formulation or a veterinary composition) or functional food composition comprising curcuminoids and optionally a pharmaceutically acceptable excipient or (functional) food acceptable ingredient, as appropriate.

A "functional food composition" as used herein refers to a nutraceutical composition, a functional food composition, a dietary or food product for humans or animals (such as functional food compositions, i.e. food, drink, feed or pet food or a food, drink, feed or pet food supplements) or a nutritional supplement. Functional food composition can be presented as beverages, dairy products, bakery products, etc.

When used in a functional food, such as a beverage, a dairy product, a bakery product, the composition of the invention is incorporated into said food product (for example in a liquid or solid form) so as to provide the effective amounts of curcuminoids (such as at least 90 mg of curcuminoids).

As used herein, references to pharmaceutically (or veterinary) acceptable excipients may refer to pharmaceutically (or veterinary) acceptable adjuvants, diluents and/or carriers as known to those skilled in the art.

Food acceptable ingredients include those known in the art (including those also referred to herein as pharmaceutically acceptable excipients) and that can be natural or non-natural, i.e. their structure may occur in nature or not. In certain instances, they can originate from natural compounds and be later modified (e.g. maltodextrin).

By "pharmaceutically acceptable" (or veterinary acceptable) we mean that the additional components of the composition are sterile and pyrogen free. Such components must be "acceptable" in the sense of being compatible with the extract of the invention and not deleterious to the recipients thereof. Thus, "pharmaceutically acceptable" includes any compound(s) used in forming a part of the formulation that is intended to act merely as an excipient, i.e. not intended to have biological activity itself. Thus, the pharmaceutically acceptable excipient is generally safe, non-toxic, and neither biologically nor otherwise undesirable. The skilled person will understand that extracts of the invention (e.g. in the form of compositions, such as pharmaceutical compositions, as known to those skilled in the art, such as those as described herein) may be administered to a patient or subject (e.g. a human or animal patient or subject) by any suitable route, such as by the oral, rectal, nasal, pulmonary, buccal, sublingual, transdermal, intracisternal, intraperitoneal, and parenteral (including subcutaneous, intramuscular, intrathecal, intravenous and intradermal) route. In particular, extracts of the invention may be administered orally. In such instances, pharmaceutical compositions according to the present invention may be specifically formulated for administration by the oral route. Suitable pharmaceutical (or veterinary) carriers include inert solid diluents or fillers, sterile aqueous solutions and various organic solvents. Examples of solid carriers are lactose, terra alba, sucrose, cyclodextrin, maltodextrin, talc, gelatin, silica, agar, pectin, acacia, magnesium stearate, stearic acid, arabic gum, modified starch and lower alkyl ethers of cellulose. Examples of liquid carriers are syrup, peanut oil, olive oil, phospholipids, fatty acids, fatty acid amines, polyoxyethyiene and water. Moreover, the carrier or diluent may include any sustained release material known in the art, such as glyceryl monostearate or glyceryl distearate, alone or mixed with a wax.

Pharmaceutical (or veterinary) compositions for oral administration include solid dosage forms such as hard or soft capsules, tablets, troches, dragees, pills, lozenges, powders and granules. Where appropriate, they can be prepared with coatings such as enteric coatings, or they can be formulated so as to provide controlled release of the active ingredient, such as sustained or prolonged release, according to methods well known in the art. Liquid dosage forms for oral administration include solutions, emulsions, aqueous or oily suspensions, syrups and elixirs.

Compositions (e.g. pharmaceutical or food compositions) described herein, such as those intended for oral administration, may be prepared according to methods known to those skilled in the art, such as by bringing the components of the composition into admixture.

Such compositions as described herein may contain one or more additional components selected from the group consisting of food ingredients, such as sweetening agents, flavouring agents, colouring agents and preserving agents. Tablets may contain the active ingredient(s) in admixture with non-toxic pharmaceutically acceptable excipients (or ingredients) which are suitable for the manufacture of tablets. These excipients (or ingredients) may, for example, be: inert diluents, such as calcium carbonate, sodium carbonate, lactose, calcium phosphate or sodium phosphate; granulating and disintegrating agents, for example, corn starch, maltodextrin or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In the methods and uses described herein, the mammal may be a human.

Because of the specific formulation of the composition comprising curcuminoids of the invention has a much better efficacy; the formulation can be formulated with lower dosages.

In a preferred embodiment the composition is formulated to provide a single dose of curcuminoids in an amount of from about 50 mg/dose, about 60 mg/dose, 70 mg/dose, 80 mg/dose, 90 mg/dose, 100 mg/dose, 150 mg/dose, 200 mg/dose 300 mg/dose, to about 1400 mg/dose, 1300 mg/dose, 1200 mg/dose, 1100 mg/dose, 1000 mg/dose, 900 mg/dose, 800 mg/dose, 700 mg/dose, 600 mg/dose, 500 mg/dose, 400 mg/dose, such as from about 70 mg/dose to about 100 mg/dose, such as about 90 mg/dose.

In a preferred embodiment of the methods/uses described herein, the composition may be formulated and/or administrated as a single dose formulation. For example, the composition may be formulated as a single dose (for example a 300 mg formulation) with a curcuminoids contain of at least 90 mg.

Moreover, because of the very high efficacy of the composition of the invention, the dosage of curcuminoids (such as the daily dose) can be also reduced.

In the methods/uses described herein, the composition may be administered or used to provide curcuminoids in an amount of from about 50 mg/day, about 60 mg/day, 70 mg/day, 80 mg/day, 90 mg/day, 100 mg/day, 150 mg/day, 200 mg/day, 300 mg/day, to about 1400 mg/day, 1300 mg/day, 1200 mg/day, 1100 mg/day, 1000 mg/day, 900 mg/day, 800 mg/day, 700 mg/day, 600 mg/day, 500 mg/day, 400 mg/day, such as from about 70 mg/day to about 100 mg/day, such as about 90 mg/day. For example, the composition may be formulated as a single dose (for example of 300 mg) with a curcuminoids contain of at least 90 mg/day.

For example, the composition may provide curcuminoids in an amount of from about 1 to about 10 mg/kg of body weight, such as from about 2.5 to about 7.5 mg/kg of body weight, such as about 5 mg/kg, or such as about 1.29 mg/kg (90 mg curcuminoids for 70 kg of body weight).

In a preferred embodiment, the dosage is of 300 mg and the daily dose of curcuminoids is from about 70 mg/day to about 150 mg/day of curcuminoids, such as from about 70 mg/day to about 100 mg/day of curcuminoids, such as about 90 mg/day of curcuminoids.

The timing and duration of administration of the composition of the invention can vary. For instance the composition may be administered before starting an exercise routine, during the exercise routine or after an exercise routine.

In an embodiment of the invention, the method of delivering is oral in liquid, solid or paste forms. Solid dosage forms for oral administration may include capsules, tablets, caplets, pills, troches, chewables, lozenges, powders, and granules. A capsule typically comprises a core material comprising a composition of the invention and a shell wall that encapsulates the core material. The core material may be solid, liquid, or an emulsion. The shell wall material may comprise soft gelatin, hard gelatin, or a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). Some such polymers may also function as taste-masking agents.

Tablets, pills, and the like may be compressed, multiply compressed, multiply layered, and/or coated. The coating may be single or multiple. In one embodiment, the coating material may comprise a polysaccharide or a mixture of saccharides and glycoproteins extracted from a plant, fungus, or microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In another embodiment, the coating material may comprise a protein. Suitable proteins include, but are not limited to, gelatin, casein, collagen, whey proteins, soy proteins, rice protein, and corn proteins. In an alternate embodiment, the coating material may comprise a fat or oil, and in particular, a high temperature melting fat or oil. The fat or oil may be hydrogenated or partially hydrogenated, and preferably is derived from a plant. The fat or oil may comprise glycerides, free fatty acids, fatty acid esters, or a mixture thereof. In still another embodiment, the coating material may comprise an edible wax. Edible waxes may be derived from animals, insects, or plants. Non-limiting examples include beeswax, lanolin, bayberry wax, carnauba wax, and rice bran wax. Tablets and pills may additionally be prepared with enteric coatings.

For example, if the final product is a beverage, the composition of the invention will be added to the final product to obtain a final dose of curcuminoids of from about 70, 80, 90, 100, 150, 200, 250 mg/day to about 1000, 900, 850, 800, 750, 700, 650, 600, 550, 500, 450, 400, 350, 300 mg/day of curcuminoids, such as from about 70 mg/day to about 150 mg/day of curcuminoids, such as from about 70 mg/day to about 90 mg/day of curcuminoids For example, the composition may provide curcuminoids in an amount of from about 1 to about 10 mg/kg of body weight, such as from about 2.5 to about 7.5 mg/kg of body weight or about 5 mg/kg, such as about 1.29 mg/kg (90 mg curcuminoids for 70 kg of body weight).

Alternatively, powders or granules embodying the compositions disclosed herein may be incorporated into a food product. In a preferred embodiment, the food product may be a drink for oral administration. Non-limiting examples of a suitable drink include fruit juice, a fruit drink, an artificially flavored drink, an artificially sweetened drink, a carbonated beverage, a sports drink, a liquid diary product, a shake, and so forth to which excipients may also be added. Other suitable means for oral administration include aqueous and nonaqueous solutions, emulsions, suspensions and solutions and/or suspensions reconstituted from non-effervescent granules, containing suitable solvents, preservatives, emulsifying agents, suspending agents, diluents, sweeteners, coloring agents, and flavoring agents. Additionally, chewable forms, as disclosed in U.S. Pat. No. 7,223,417, incorporated herein wholly by reference, may be used.

The beverage products disclosed here optionally contain a flavor composition, i.e., one or more flavor components, for example, natural or synthetic fruit flavors, botanical flavors, other flavors, and mixtures of any of them. As used here, the term "fruit flavor" refers generally to those flavors derived from the edible reproductive part of a seed plant. Included are both those wherein a sweet pulp is associated with the seed, e.g., banana, tomato, cranberry and the like, and those having a small, fleshy berry. The term berry also is used here to include aggregate fruits, i.e., not "true" berries, but those that are commonly accepted as a berry. Also included within the term "fruit flavor" are synthetically prepared flavors made to simulate fruit flavors derived from natural sources. Examples of suitable fruit or berry sources include whole berries or portions thereof, berryjuice, berryjuice concentrates, berry purees and blends thereof, dried berry powders, dried berry juice powders, and the like.

The compositions may also be a solid foodstuff. Suitable examples of a solid foodstuff include a food bar, gummies, a snack bar, a cookie, a brownie, a muffin, a cracker, a chewable gum, an ice cream bar, a frozen yogurt bar, a chewy snack and the like. In an embodiment, the method comprises administering the composition as described above multiple times per day, or if taken as a liquid, may be mixed and taken throughout the day.

In an alternative or further embodiment of a method of delivery, the composition may also be used in conjunction with exercise. For example, the composition may be given before, during or immediately after exercise. In such embodiments, the composition may be in the form for example of sports drinks.

Typically the period of administration of the composition of the invention comprising curcuminoids (such as in a pharmaceutical or food composition comprising curcuminoids) in the uses of methods of the invention described herein, is of more than 2 days, more than 3 days more than 4 days, more than 5 days, more than 6 days, more than 7 days; more than 1 week, more than 2 weeks, more than 3 weeks, more than 4 weeks, more than 5 weeks, more than 6 weeks, more than 7 weeks, more than 8 weeks, more than 9 weeks, more than 10 weeks, more than 1 month, more than 1 months, more than 2 months, more than 3 months, more than 4 months, more than 5 months, more than 6 months, more than 7 months, more than 8 months, more than 9 months, more than 10 months, more than 11 months, more than 12 months.

"Subject" refers to a human or non-human animal, including, but not limited to, mice, rats, rabbits, dogs, cats, pigs, cows, and non-human primates, including, but not limited to, monkeys and chimpanzees. In a preferred embodiment the subject is a human (female or male).

"Administration" or "administering" refers to routes of introducing a compound or composition provided herein to an individual to perform its intended function. An example of a route of administration that can be used includes, but is not limited to oral, parenteral administration, such as subcutaneous, intravenous, or intramuscular injection or infusion, etc.

"Healthy subject" refers to an individual who is not known to suffer of any significant illness and corresponds to the general population.

As used herein, the term "treatment" (and, similarly, "treating") takes its normal meaning in the field of medicine. In particular, the term may refer to achieving a reduction (for example, at least a 10% reduction, such as at least a 20%, 30% or 40% reduction, e.g. at least a 50% reduction) in the severity of one or more clinical symptom associated with the disease or disorder (e.g. muscle soreness such as muscle pain), as may be determined using techniques known to those skilled in the art (for example, by a medical physician) or the ones descried in the examples and/or to slowing the progression of the disease or disorder (i.e. increasing the amount of time taken for the disease or disorder to progress to a more severe state, e.g. when compared to the time expected to be taken in a patent not so treated). As used herein, the term "prevention" (and, similarly, "preventing") includes references to the prophylaxis of the disease or disorder (and vice-versa). In particular, the term may refer to achieving a reduction in the likelihood of the patient (or healthy subject) developing the condition (for example, at least a 10% reduction, such as at least a 20%, 30% or 40% reduction, e.g. at least a 50% reduction).

As used herein in relation to medical conditions, the term "reducing" may refer to making the observed quantity smaller or decrease in size (i.e. reducing the muscle pain, reducing CK levels in blood). In particular, the term may refer to achieving a reduction in the likelihood of the patient (or healthy subject) developing the condition (for example, at least a 10% reduction, such as at least a 20%, 30% or 40% reduction, e.g. at least a 50% reduction).

The treating or reduction achieved by the compositions of the invention, may be obtained after 24 h or ingestion, or after 48 h, after 72 h, after 4 days, after 5 days, after 1 week or the consumption of the composition of the invention.

For the avoidance of doubt, preferences, options, particular features and the like indicated for a given aspect, feature or parameter of the invention should, unless the context indicates otherwise, be regarded as having been disclosed in combination with any and all other preferences, options particular features and the like as indicated for the same or other aspects, features and parameters of the invention.

The term "about" as used herein, e.g. when referring to a measurable value (such as an amount or weight of a particular component in the reaction mixture), refers to variations of ±20%, ±10%, ±5%, ±1%, ±0.5%, or, particularly, ±0.1% relative to the specified amount. For example, a variation of ±0.5% with regards to the percentage of a component in the composition of the invention, means a variation of 0.5% relative to the percentage given, i.e. ±0.5% of 10% would mean a variation from 9.5% to 10.5%.

EXAMPLES

Test Formulation

The Test Formulation is composed of: natural powdered extract obtained from Turmeric (*Curcuma longa*) root, Acacia gum, Sunflower oil and *Quillaja* extract. It has been developed and is intended for use as a food supplement. It has already been tested for safety in pre-clinical and human studies.

The formulation is: 30-40% of *Curcuma longa* rhizome ethanol extract, 55-65% acacia gum, 3-7%, sunflower oil, 1-3% *quillaja* extract. The *quillaja* component is an extract powder containing approximately 65% saponins by dry weight.

The Curcuminoids content is of 30% w/w, curcumin content 23% (w/w) and about 7% (w/w) of DMC and BDMC w/w (in respect to total weight).

The primary objective of this study is to evaluate for the males the difference of a five-day supplementation effect of the Turmipure GOLD® (test Formulation) versus Placebo on exercise-induced muscle pain within 72 hours post-exercise. Evaluations are performed at Baseline (before and after damaging exercise) and every 24 h for 3 days using VAS (0-100 mm) for perceived muscle soreness in quadriceps during squatting activities (after two tries).

Secondary objectives are to evaluate a five-day supplementation of Turmipure GOLD® (test Formulation) versus Placebo on the following outcomes within 72 hours post-exercise (evaluations are performed at Baseline (before and after damaging exercise) and every 24 h for 3 days):

- the difference of the effect for the totality of subjects (males and females) on exercise-induced muscle pain using VAS (0-100 mm) for perceived muscle soreness in quadriceps during squatting activities (after two tries);
- the difference of the effect for the males and the totality of subjects (males and females) on exercise-induced muscle damage assessed by circulating levels of Creatine kinase in blood samples;
- the difference of the effect for the males and the totality of subjects (males and females) on muscular function recovery through: isometric and isokinetic quadriceps muscular function (recording the torque, power, and work capacity using Biodex during knee extension), peak power (during vertical jump tests recording height, velocity, and power for the best performance and average of 3 tries), and range of motion (using a goniometer during knee flexion);
- the difference of the effect for the males and the totality of subjects (males and females) on perceived wellness and wellbeing (assessed by a psychometric test evaluating fatigue, sleep quality, general muscle soreness, stress, and mood);
- the difference of the effect for the males and the totality of subjects (males and females) of supplementation with Turmipure Gold® (test Formulation) versus Placebo on perceived exertion (during exercise).

This is a superiority study (trial to determine difference). Therefore, primary hypothesis will aim to demonstrate the superiority of Turmipure Gold® (test Formulation) over Placebo for improving exercise-induced muscle pain and function recovery in moderately active adults.

Sample size calculation is based on previous similar studies (Xia, Z., J. M. Cholewa, D. Dardevet, T. Huang, Y. Zhao, H. Shang, Y. Yang, et al. 2018. "Effects of Oat Protein Supplementation on Skeletal Muscle Damage, Inflammation and Performance Recovery Following Downhill Running in Untrained Collegiate Men." Food and Function 9 (9): 4720-29;) and aim to compare the Area Under the Curve (AUC) for each parameter experimented immediately before and after the damaging exercise and for 24, 48 and 72 hrs between Turmipure Gold (test Formulation) and Placebo groups. A total of 29 evaluable subjects by treatment groups will be necessary to ensure a 80% power to detect a significant difference between Turmipure Gold® (test Formulation) and Placebo for two-sided test at the 5% level. Assuming a 15% of non-evaluable subjects by group, up to a total of 35 male subjects per group may be randomized. Additionally, 10 females will also be included but were not considered for sample size calculations.

The study is a randomized, double-blinded, placebo controlled, crossover trial. According to their randomization, participants are randomly allocated to one of the two groups of this crossover study to determine the 5-days dosing sequence of Turmipure Gold® (test Formulation) and Placebo products. One group consume the new test product (test Formulation) during the first phase and Placebo during the second phase and, the second group consume the Placebo during the first phase and the new test product (test Formulation) during the second phase.

Participants are instructed to take either Turmipure GOLD® (test Formulation) (300 mg) or placebo (300 mg) daily for 5 days>1 capsule/once a day.

1—Group TPG/Placebo: 300 mg/per capsule of (Phase 1) Turmipure GOLD® (TPG) Test Formulation and 300 mg/percapsule (Phase 2) of Dyed Acacia Gum.

2—Group Placebo/TPG: 300 mg/per capsule of (Phase 2) Turmipure GOLD® (TPG) Test Formulation and 300 mg/percapsule (Phase 1) of Dyed Acacia Gum.

Participants are enrolled in the study if they fulfill all inclusion criteria and present none of the exclusion criteria. Ethical approval was given from the ethics committee of Cork (Ireland).

Participants are included in the study if they fulfill all the following criteria:

1. Healthy free-living males and females.
2. Age: 25-45 years old.
3. Have a BMI between 18.5 and 28 kg/$m^2$.
4. Moderately active with running 15-20 km per week.
5. With 1 to 4 h of training per week, with maximum 1 h of lower body heavy-load or resistance training (e.g., Hill running or hiking, HIT exercise, Squats, Lunges, Leg-press, Bench steps, etc.).
6. Consent to the study protocol and to comply with study product.
7. Willing to limit caffeine, smoking, and alcohol consumption during the entire study period with no more than 5 cigarettes per day and 1.5 or 2 drinks respectively for women and men. Also, alcohol consumption will not be allowed 24 hours prior to exercise-induced muscular damage.
8. Willing to refrain from training for 3 days before the first test, 5 days before each damage-inducing exercise and during each supplementation phase, including active recovery exercises such as swimming, cycling at low intensity, unusual distance walking (however such should be encouraged during the 14 days wash-out).
9. Willing to refrain the use of anti-inflammatory/pain reliever drugs such as paracetamol, NSAIDs, etc., during each supplementation phase, from 24 hours prior to 72 hours following the exercise-induced muscular damage.
10. Willing to refrain from 'recovery' treatments over the 72 hours following the damage inducing exercise such as:
    a. Hydrotherapy—cold water immersion, hot water immersion, or contrast therapy (as well as Jacuzzis, Steam baths, or Saunas)
    b. Massage—self, foam rolling, etc.
    c. Stretching
    d. Compression garments
    e. Topical applications—Tiger Balm, Deep Heat etc.

Participants are excluded if they present at least one of the following criteria:

1. Participants with any indicators of arthritis, joint disorders chronic pain syndrome, muscle disorder diseases (e.g., fibromyalgia, etc.).
2. History of surgery or significant injury in joints or in the lower limb in the last six months prior to study enrolment, or an anticipated need for surgical or invasive procedure that will be performed during the study.
3. Using omega-3-fatty acid, probiotic supplements, vitamins, minerals, or any dietary supplements (including botanicals), especially to maintain joint health 4 weeks prior to screening and during the entire study. Potential supplements include but are not limited to Beta-alanine, Creatine, HMB, Carnosine, Taurine, androstenedione, DHEA, Whey protein, or a pre-workout supplement.
4. Following any specific diet such as high-protein, vegetarian, vegan, etc.
5. Taking any drugs such as antibiotics, laxatives, or immunosuppressant drugs.
6. History of glucocorticoid injection or hyaluronic acid injections within 3 months prior to enrolment
7. Participants near or in the peak of training for an athletic race (half or marathon, cycling tour or triathlon).
8. History or current significant cardiovascular, pulmonary, renal, liver, digestive (including an inflammatory bowel disease), infectious disease, systemic disease, immune disorder, or metabolic/endocrine disorders (including diabetes mellitus) or other disease that would preclude supplement ingestion and/or assessment of study objectives, including uncontrolled hypertension, uncontrolled thyroidism or lipidaemia that is not on stable medication for at least 3 months.
9. Participant has any concurrent medical or psychiatric condition that, in the opinion of the Investigator, would compromise his/her ability to comply with the study requirements.
10. Participant with history of drug and/or alcohol abuse at the time of enrolment.
11. Any previous or current cancer diagnosis (including a benign or malign tumor of intestine or colon).
12. Current illnesses which could interfere with the study (e.g., prolonged severe diarrhea, regurgitation/severe, difficulty swallowing).
13. Known allergy to components of the test product or sensitivity to herbal products or with a medical history of food allergies.
14. Participants taking any anticoagulant or heparin treatment (including aspirin).
15. Pregnant or lactating females.
16. Clinically significant abnormal laboratory results at screening.
17. Participant currently involved in any other clinical trial or having participated in a trial within 90 days prior to randomisation.
18. Any other condition which in the Investigator's opinion may adversely affect the subject's ability to complete the study or its measures or which may pose significant risk to the subject.

19. History of non-compliance with medical treatments or recommendations.

20. Participants who are required to perform squatting motions or descend a lot of stairs in their daily work activities, which may be painful following the Exercise Induced Muscle Damage.

In order to evaluate for nutrient intake in the participant's diet, a food questionnaire (5-Day Food Diary) is performed during the complete supplementation phases of the study.

In order to evaluate for participant's physical activity, an activity questionnaire (IPAQ) is performed at baseline (before damaging exercise) of each supplementation phase.

In order to evaluate for female hormonal cycle, female participants who menstruate complete a menstruation questionnaire.

The perceived muscle soreness in quadriceps assessed by VAS (visual analogue scale 0-100 mm) between treatment groups is determined using the AUC0-72 hrs (area under the curve from measurements pre- and directly, 24 h, 48 h, 72 h post-exercise) analysis of each supplementation phase. The muscular recovery/function/power/strength assessed by (1) Isometric and isokinetic quadriceps muscular function recording the torque, power, and work capacity using Biodex (knee extension, best performance and average of 3 tries); (2) Peak power using vertical jump tests recording height, velocity, and power (best performance and average of 3 tries); (3) Range of movement using a goniometer (knee flexion) is determined using the AUC0-72 hrs (area under the curve from measurements pre- and directly, 24 h, 48 h, 72 h post-exercise) analysis of each supplementation phase.

The perceived wellness and wellbeing assessed by a psychometric test evaluating fatigue, sleep quality, general muscle soreness, stress, and mood (see table 1) is determined using the AUC0-72 hrs (area under the curve from measurements pre- and directly, 24 h, 48 h, 72 h post-exercise) analysis of each supplementation phase. (Hooper S L et al. Sport Med. 1995; 20(5): 321-327, Buchheit M. et al, J. Sci. Med. Sport. 2013; 16(6):550-5).

FIG. 1. Psychometric test for assessment of perceived wellness and wellbeing.

The perceived exertion assessed by the Borg Rating of Perceived Exertion is determined by change from baseline values obtained during exercise of each supplementation phase (M. H Milot et al Clin Interv Aging 2019; 14:9-16).

Between-group difference is evaluated using a statistical mixed model on repeated measure (MMRM) including treatment group, sequence, supplementation phase as fixed effects and subject nested sequence as random effect. The differences of primary and secondary outcomes is evaluated using appropriated analysis and if required covariates (e.g. baseline activity level or diet).

The following tables display data for 33-34 participants.

TABLE 1

Pain assessment of the quadriceps after two squats using VAS (0-100 mm) before exercise, after two doses of treatment (the day before and the same day as the exercise)

| | TPG | | Placebo | | % difference Placebo > | p |
|---|---|---|---|---|---|---|
| Variable | Mean | SD | Mean | SD | TPG | value |
| Before exercise | 6.59 | 7.98 | 9.53 | 10.71 | 44.61 | <0.0001 |

TABLE 2

AUC values over 72 h pre-post exercise for pain assessment of the quadriceps after two squats using VAS (0-100 mm), after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| AUC 0-72h | 1796.2 | 997.54 | 1929.12 | 1350.08 | 7.40 |

TABLE 3

AUC values over 72 h pre-post exercise for blood Creatine kinase (U/L), after five doses of treatment (the day before and the same day as the exercise, as well as 24 h, 48 h and 72 h post exercise)

| Variable | TPG Median | Placebo Median | % difference Placebo > TPG |
|---|---|---|---|
| AUC 0-72 h | 19382.7 | 25128.3 | 29.64 |

TABLE 4

AUC values over 72 h pre-post exercise for Isokinetic Peak Torque (Nm) as the best of 3 trials on dominant leg, after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| AUC 0-72 h | 13711.14 | 2804.06 | 13551.04 | 2825.52 | −1.17 |

TABLE 5

Changes from baseline (pre-exercise) at 0 h, 24 h, 48 h and 72 h post exercise for Isokinetic Peak Torque (Nm) as the best of 3 trials on dominant leg, after five doses of treatment (the day before and the same day as the exercise, as well as 24 h, 48 h and 72 h post exercise)

| Variable | TPG Median | Placebo Median | % difference Placebo > TPG |
|---|---|---|---|
| Post exercise | −8.1 | −16.25 | 100.62 |
| 24 h | −12.65 | −15.5 | 22.53 |
| 48 h | −7.35 | −15.65 | 112.93 |
| 72 h | −4.6 | −5.9 | 28.26 |

TABLE 6

AUC values over 72 h pre-post exercise for Isokinetic Peak Torque (Nm) as the average of 3 trials on dominant leg, after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| AUC 0-72 h | 13118.29 | 2819.37 | 13030.6 | 2811.04 | −0.67 |

TABLE 7

Changes from baseline (pre-exercise) at 0 h, 24 h and 48 h post exercise for Isokinetic Peak Torque (Nm) as the average of 3 trials on dominant leg, after two, three and four doses of treatment (the day before and the same day as the exercise, as well as 24 h and 48 h post exercise)

| Variable | TPG Median | Placebo Median | % difference Placebo > TPG |
|---|---|---|---|
| Post exercise | −9.85 | −11.25 | 14.21 |
| 24 h | −14.35 | −17.3 | 20.56 |
| 48 h | −12.85 | −16.25 | 26.46 |

TABLE 8

AUC values over 72 h pre-post exercise for Isokinetic Max Rep Work (J) as the best of 3 trials on dominant leg, after five doses of treatment (the day before and the same day as the exercise, as well as 24 h, 48 h and 72 h post exercise)

| Variable | TPG Median | Placebo Median | % difference Placebo > TPG |
|---|---|---|---|
| AUC 0-72 h | 14645.59 | 14152.35 | −3.37 |

TABLE 9

Changes from baseline (pre-exercise) at 0 h, 24 h, 48 h and 72 h post exercise for Isokinetic Max Rep Work (J) as the best of 3 trials on dominant leg, after five doses of treatment (the day before and the same day as the exercise, as well as 24 h, 48 h and 72 h post exercise)

| | TPG | | Placebo | | % difference Placebo > | p |
|---|---|---|---|---|---|---|
| Variable | Mean | SD | Mean | SD | TPG | value |
| Post exercise | −18.25 | 17.59 | −22.12 | 24.2 | 21.21 | 0.0055 |
| 24 h | −11.06 | 19.02 | −21.73 | 30.72 | 96.47 | |
| 48 h | −16.37 | 26.46 | −18.89 | 28.61 | 15.39 | |
| 72 h | −5.92 | 22.41 | −12.45 | 28.19 | 110.30 | |

TABLE 10

AUC values over 72 h pre-post exercise for Isokinetic Max Rep Work (J) as the average of 3 trials on dominant leg, after five doses of treatment (the day before and the same day as the exercise, as well as 24 h, 48 h and 72 h post exercise)

| Variable | TPG Median | Placebo Median | % difference Placebo > TPG |
|---|---|---|---|
| AUC 0-72 h | 14132.89 | 13576.88 | −3.93 |

TABLE 11

Changes from baseline (pre-exercise) at 0 h, 24 h, 48 h and 72 h post exercise for Isokinetic Max Rep Work (J) as the average of 3 trials on dominant leg, after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| Post exercise | −16.98 | 18.48 | −22.12 | 23.94 | 30.27 |
| 24 h | −12.51 | 21.17 | −20.17 | 29.81 | 61.23 |
| 48 h | −16.87 | 27.35 | −19.23 | 29.23 | 13.99 |
| 72 h | −7.46 | 24.58 | −12.37 | 28.89 | 65.82 |

TABLE 12

AUC values over 72 h pre-post exercise for Isokinetic Power (W) as the best of 3 trials on dominant leg, after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| AUC 0-72 h | 8759.92 | 1923.12 | 8642.87 | 2003.09 | −1.34 |

TABLE 13

Changes from baseline (pre-exercise) at 0 h, 24 h, 48 h and 72 h post exercise for Isokinetic Power (W) as the best of 3 trials on dominant leg, after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| Post exercise | −8.56 | 11.79 | −11.18 | 15.37 | 30.61 |
| 24 h | −7.06 | 11.13 | −12.59 | 19.53 | 78.33 |
| 48 h | −9.18 | 17.05 | −10.48 | 19.24 | 14.16 |
| 72 h | −1.56 | 18.74 | −5.72 | 18.72 | 266.67 |

TABLE 14

AUC values over 72 h pre-post exercise for Isokinetic Power (W) as the average of 3 trials on dominant leg, after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| AUC 0-72 h | 8400.51 | 1906.51 | 8317.79 | 1992.64 | −0.98 |

TABLE 15

Changes from baseline (pre-exercise) at 0 h, 24 h, 48 h and 72 h post exercise for Isokinetic Power (W) as the average of 3 trials on dominant leg, after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| Post exercise | −7.5 | 12.2 | −10.78 | 14.89 | 43.73 |
| 24 h | −7.63 | 12.99 | −11.56 | 18.41 | 51.51 |
| 48 h | −8.86 | 17.03 | −10.29 | 19.12 | 16.14 |
| 72 h | −2.49 | 16.07 | −5.76 | 18.83 | 131.33 |

TABLE 16

AUC values over 72 h pre-post exercise for Isometric Peak Torque (Nm) as the best of 3 trials on dominant leg, after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| AUC 0-72 h | 16944.38 | 4196.49 | 16589.16 | 3918.55 | −2.10 |

TABLE 17

Changes from baseline (pre-exercise) at 0 h, 24 h, 48 h and 72 h post exercise for Isometric Peak Torque (Nm) as the best of 3 trials on dominant leg, after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| Post exercise | −23.15 | 23.79 | −31.86 | 28.26 | 37.62 |
| 24 h | −7.59 | 29.48 | −11.43 | 38.6 | 50.59 |
| 48 h | −10.9 | 31.68 | −17.49 | 31.88 | 60.46 |
| 72 h | 3.08 | 33.96 | −0.24 | 30.05 | na |

TABLE 18

AUC values over 72 h pre-post exercise for Isometric Peak Torque (Nm) as the average of 3 trials on dominant leg, after five doses of treatment (the day before and the same day as the exercise, as well as 24 h, 48 h and 72 h post exercise)

| | TPG | | Placebo | | % difference |
|---|---|---|---|---|---|
| Variable | Mean | SD | Mean | SD | Placebo > TPG |
| AUC 0-72 h | 16323.7 | 4107.56 | 15910.48 | 3903.2 | −2.53 |

TABLE 19

Changes from baseline (pre-exercise) at 0 h, 24 h, 48 h and 72 h post exercise for Isometric Peak Torque (Nm) as the average of 3 trials on dominant leg, after five doses of treatment (the day before and the same day as the exercise, as well as 24 h, 48 h and 72 h post exercise)

| | TPG | | Placebo | | % difference Placebo > | p |
|---|---|---|---|---|---|---|
| Variable | Mean | SD | Mean | SD | TPG | value |
| Post exercise | −22.83 | 27.98 | −30.58 | 24.68 | 33.95 | 0.0146 |
| 24 h | −7.94 | 29.69 | −10.75 | 33.92 | 35.39 | |
| 48 h | −9.26 | 31.68 | −15.54 | 31.05 | 67.82 | |
| 72 h | 3.72 | 35.65 | 0.45 | 30.43 | −87.90 | |

TABLE 20

Muscle power assessment with Peak Power Score (W) before exercise as the best of 3 trials of vertical jumps, after two doses of treatment (the day before and the same day as the exercise)

| | TPG | | Placebo | | % difference Placebo > | p |
|---|---|---|---|---|---|---|
| Variable | Mean | SD | Mean | SD | TPG | value |
| Before exercise | 931.64 | 140.06 | 925.06 | 143.77 | −0.71 | <0.0001 |

TABLE 21

| | TPG | | Placebo | | % difference |
|---|---|---|---|---|---|
| Variable | Mean | SD | Mean | SD | Placebo > TPG |
| AUC 0-72 h | 68287.74 | 10103.27 | 67465.46 | 10723.1 | −1.20 |

AUC values over 72 h pre-post exercise for Peak Power Score (W) as the best of 3 trials of vertical jumps, after five doses of treatment (the day before and the same day as the exercise, as well as 24 h, 48 h and 72 h post exercise)

TABLE 22

| Variable | TPG Median | Placebo Median | % difference Placebo > TPG |
|---|---|---|---|
| 24 h | −3.3 | −21.1 | 539.39 |
| 48 h | 2.8 | −5.65 | na |

Changes from baseline (pre-exercise) at 24 h and 48 h post exercise for Peak Power Score (W) as the best of 3 trials of vertical jumps, after three and four doses of treatment (the day before and the same day as the exercise, as well as 24 h and 48 h post exercise)

TABLE 23

Muscle power assessment with Peak Power Score (W) before exercise as the average of 3 trials of vertical jumps, after two doses of treatment (the day before and the same day as the exercise)

| | TPG | | Placebo | | % difference Placebo > | p |
|---|---|---|---|---|---|---|
| Variable | Mean | SD | Mean | SD | TPG | value |
| Before exercise | 921.79 | 139.67 | 916.09 | 143.55 | −0.62 | <0.0001 |

TABLE 24

| | TPG | | Placebo | | % difference |
|---|---|---|---|---|---|
| Variable | Mean | SD | Mean | SD | Placebo > TPG |
| AUC 0-72 h | 67517.95 | 9989.93 | 66753.78 | 10676.66 | −1.13 |

AUC values over 72 h pre-post exercise for Peak Power Score (W) as the average of 3 trials of vertical jumps, after five doses of treatment (the day before and the same day as the exercise, as well as 24 h, 48 h and 72 h post exercise)

TABLE 25

| Variable | TPG Median | Placebo Median | % difference Placebo > TPG |
|---|---|---|---|
| 24 h | −3.15 | −16.2 | 414.29 |
| 48 h | 3.2 | −6.9 | na |

Changes from baseline (pre-exercise) at 24 h and 48 h post exercise for Peak Power Score (W) as the average of 3 trials of vertical jumps, after three and four doses of treatment (the day before and the same day as the exercise, as well as 24 h and 48 h post exercise)

TABLE 26

Muscle function assessment with Height (cm) before exercise as the best of 3 trials of vertical jumps, after two doses of treatment (the day before and the same day as the exercise)

| | TPG | | Placebo | | % difference Placebo > | p |
|---|---|---|---|---|---|---|
| Variable | Mean | SD | Mean | SD | TPG | value |
| Before exercise | 27.42 | 4.77 | 27.25 | 5.51 | −0.62 | <0.0001 |

TABLE 27

| | TPG | | Placebo | | % difference |
|---|---|---|---|---|---|
| Variable | Mean | SD | Mean | SD | Placebo > TPG |
| AUC 0-72 h | 2003.16 | 357.71 | 1979.17 | 419.99 | −1.20 |

AUC values over 72 h pre-post exercise for Height (cm) as the best of 3 trials of vertical jumps, after five doses of treatment (the day before and the same day as the exercise, as well as 24 h, 48 h and 72 h post exercise)

TABLE 28

| | TPG | | Placebo | | % difference |
|---|---|---|---|---|---|
| Variable | Mean | SD | Mean | SD | Placebo > TPG |
| 24 h | −0.04 | 1.57 | −1.09 | 2.11 | 2625.00 |
| 48 h | −0.07 | 1.86 | −0.83 | 2.47 | 1085.71 |

Changes from baseline (pre-exercise) at 24 h and 48 h post exercise for Height (cm) as the best of 3 trials of vertical jumps, after three and four doses of treatment (the day before and the same day as the exercise, as well as 24 h and 48 h post exercise)

TABLE 29

Muscle function assessment with Height (cm) before exercise as the average of 3 trials of vertical jumps, after two doses of treatment (the day before and the same day as the exercise)

| | TPG | | Placebo | | % difference Placebo > | p |
|---|---|---|---|---|---|---|
| Variable | Mean | SD | Mean | SD | TPG | value |
| Before exercise | 26.82 | 4.74 | 26.73 | 5.5 | −0.34 | <0.0001 |

TABLE 30

| | TPG | | Placebo | | % difference |
|---|---|---|---|---|---|
| Variable | Mean | SD | Mean | SD | Placebo > TPG |
| AUC 0-72 h | 1960.69 | 350.29 | 1940.35 | 419.36 | −1.04 |

AUC values over 72 h pre-post exercise for Height (cm) as the average of 3 trials of vertical jumps, after five doses of treatment (the day before and the same day as the exercise, as well as 24 h, 48 h and 72 h post exercise)

TABLE 31

| | TPG | | Placebo | | % difference |
|---|---|---|---|---|---|
| Variable | Mean | SD | Mean | SD | Placebo > TPG |
| 24 h | −0.38 | 1.56 | −1.08 | 2.08 | 184.21 |
| 48 h | −0.1 | 1.82 | −0.78 | 2.35 | 680.00 |

Changes from baseline (pre-exercise) at 24 h and 48 h post exercise for Height (cm) as the average of 3 trials of vertical jumps, after three and four doses of treatment (the day before and the same day as the exercise, as well as 24 h and 48 h post exercise)

TABLE 32

Muscle function assessment with Velocity (m/s) before exercise as the best of 3 trials of vertical jumps, after two doses of treatment (the day before and the same day as the exercise)

| | TPG | | Placebo | | % difference Placebo > | p |
|---|---|---|---|---|---|---|
| Variable | Mean | SD | Mean | SD | TPG | value |
| Before exercise | 2.311 | 0.198 | 2.302 | 0.231 | −0.39 | <0.0001 |

TABLE 33

| | TPG | | Placebo | | % difference |
|---|---|---|---|---|---|
| Variable | Mean | SD | Mean | SD | Placebo > TPG |
| AUC 0-72 h | 169.219 | 14.996 | 167.871 | 18.027 | −0.80 |

AUC values over 72 h pre-post exercise for Velocity (m/s) as the best of 3 trials of vertical jumps, after five doses of treatment (the day before and the same day as the exercise, as well as 24 h, 48 h and 72 h post exercise)

TABLE 34

| | TPG | | Placebo | | % difference |
|---|---|---|---|---|---|
| Variable | Mean | SD | Mean | SD | Placebo > TPG |
| 24 h | −0.019 | 0.07 | −0.049 | 0.091 | 157.89 |
| 48 h | −0.004 | 0.08 | −0.043 | 0.123 | 975.00 |

Changes from baseline (pre-exercise) at 24 h and 48 h post exercise for Velocity (m/s) as the best of 3 trials of vertical jumps, after three and four doses of treatment (the day before and the same day as the exercise, as well as 24 h and 48 h post exercise)

TABLE 35

| | TPG | | Placebo | | % difference |
|---|---|---|---|---|---|
| Variable | Mean | SD | Mean | SD | Placebo > TPG |
| Before exercise | 2.285 | 0.199 | 2.278 | 0.232 | −0.31 |

Muscle function assessment with Velocity (m/s) before exercise as the average of 3 trials of vertical jumps, after two doses of treatment (the day before and the same day as the exercise)

TABLE 36

| | TPG | | Placebo | | % difference |
|---|---|---|---|---|---|
| Variable | Mean | SD | Mean | SD | Placebo > TPG |
| AUC 0-72 h | 169.592 | 18.299 | 166.148 | 18.234 | −2.03 |

AUC values over 72 h pre-post exercise for Velocity (m/s) as the average of 3 trials of vertical jumps, after five doses of treatment (the day before and the same day as the exercise, as well as 24 h, 48 h and 72 h post exercise)

TABLE 37

| | TPG | | Placebo | | % difference |
|---|---|---|---|---|---|
| Variable | Mean | SD | Mean | SD | Placebo > TPG |
| 24 h | −0.017 | 0.071 | −0.048 | 0.091 | 182.35 |
| 48 h | −0.005 | 0.078 | −0.041 | 0.12 | 720.00 |
| 72 h | 0.197 | 1.027 | 0.027 | 0.102 | −86.29 |

Changes from baseline (pre-exercise) at 24 h, 48 h and 72 h post exercise for Velocity (m/s) as the average of 3 trials of vertical jumps, after three, four and five doses of treatment (the day before and the same day as the exercise, as well as 24 h, 48 h and 72 h post exercise)

TABLE 38

| Variable | TPG Median | Placebo Median | % difference Placebo > TPG |
|---|---|---|---|
| AUC 0-72 h | 10118.3 | 10041 | −0.76 |

AUC values over 72 h pre-post exercise for Range of motion (degrees) during knee flexion on dominant leg, after five doses of treatment (the day before and the same day as the exercise, as well as 24 h, 48 h and 72 h post exercise)

TABLE 39

| | TPG | | Placebo | | % difference |
|---|---|---|---|---|---|
| Variable | Mean | SD | Mean | SD | Placebo > TPG |
| 72 h | 0.9 | 3 | −0.4 | 3.2 | na |

Changes from baseline (pre-exercise) at 72 h post exercise for Range of motion (degrees) during knee flexion on dominant leg, after five doses of treatment (the day before and the same day as the exercise, as well as 24 h, 48 h and 72 h post exercise)

As we can see in Table 1, placebo treated group had significantly more pain (+44.61%) than the test Formulation of the invention (TPG) treated group during squat performance.

As we can see in Tables 20, 26 and 32, placebo treated group shows significantly less power, height and velocity (respectively −0.71%, −0.62% and −0.39% for the best jump) than the test Formulation of the invention (TPG) treated group during vertical jump performance. This is confirmed in Tables 23, 29 and 35 with significantly less power (−0.62%) and less height (−0.34%), as well as a tendency for less velocity (−0.31%) while compiling the average of three jumps.

As we can see in Table 2, placebo treated group had more pain (+7.4%) than the test Formulation of the invention (TPG) treated group during squat performance during the overall five-day evaluation (comparing before and after downhill exercise).

As we can see in Table 3, placebo treated group shows more blood creatine kinase (+29.64%) than the test Formulation of the invention (TPG) treated group during the overall five-day evaluation (comparing before and after downhill exercise).

As we can see in Tables 4 and 6, placebo treated group shows lower isokinetic peak torque (Nm) levels (−1.17% and −0.67%, respectively considering the best or the average of three trials) than the test Formulation of the invention (TPG) treated group during the overall five-day evaluation (comparing before and after downhill exercise). In Table 5, test Formulation of the invention (TPG) group shows lower isokinetic peak torque (Nm) loss with +100.62%, +22.53%, +112.93% and +28.26% differences for the placebo group (changes from baseline respectively compared directly, 24 h, 48 h and 72 h after downhill exercise), considering the best of 3 trials. In Table 7, test Formulation of the invention (TPG) group shows lower isokinetic peak torque (Nm) loss with +14.21%, +20.56% and +26.46% differences for the placebo group (changes from baseline respectively compared directly, 24 h and 48 h after downhill exercise), considering the average of 3 trials. As we can see in Tables 8 and 10, placebo treated group shows lower isokinetic max rep work (J) levels (−3.37% and −3.93%, respectively considering the best or the average of three trials) than the test Formulation of the invention (TPG) treated group during the overall five-day evaluation (comparing before and after downhill exercise). In Table 9, test Formulation of the invention (TPG) group significantly shows lower isokinetic max rep work (J) loss with +21.21%, +96.47%, +15.39% and +110.30% differences for the placebo group (changes from baseline respectively compared directly, 24 h, 48 h and 72 h after downhill exercise), considering the best of 3 trials. In Table 11, test Formulation of the invention (TPG) group shows lower isokinetic max rep work (J) loss with +30.27%, +62.23%, +13.99% and +65.82% differences for the placebo group (changes from baseline respectively compared directly, 24 h, 48 h and 72 h after downhill exercise), considering the average of 3 trials.

As we can see in Tables 12 and 14, placebo treated group shows lower isokinetic power (W) levels (−1.34% and −0.98%, respectively considering the best or the average of three trials) than the test Formulation of the invention (TPG) treated group during the overall five-day evaluation (comparing before and after downhill exercise). In Table 13, test Formulation of the invention (TPG) group shows lower isokinetic power (W) loss with +30.61%, +78.33%, +14.16% and +266.67% differences for the placebo group (changes from baseline respectively compared directly, 24 h, 48 h and 72 h after downhill exercise), considering the best of 3 trials. In Table 15, test Formulation of the invention (TPG) group shows lower isokinetic power (W) loss with 30.27%, 62.23%, 13.99% and 65.82% differences with the placebo group (changes from baseline respectively compared directly, 24 h, 48 h and 72 h after downhill exercise), considering the average of 3 trials.

As we can see in Tables 12 and 14, placebo treated group shows lower isokinetic power (W) levels (−1.34% and −0.98%, respectively considering the best or the average of three trials) than the test Formulation of the invention (TPG) treated group during the overall five-day evaluation (comparing before and after downhill exercise). In Table 13, test Formulation of the invention (TPG) group shows lower isokinetic power (W) loss with +30.61%, +78.33%, +14.16% and +266.67% differences for the placebo group (changes from baseline respectively compared directly, 24 h, 48 h and 72 h after downhill exercise), considering the best of 3 trials. In Table 15, test Formulation of the invention (TPG) group shows lower isokinetic power (W) loss with 30.27%, 62.23%, 13.99% and 65.82% differences with the placebo group (changes from baseline respectively compared directly, 24 h, 48 h and 72 h after downhill exercise), considering the average of 3 trials.

As we can see in Tables 12 and 14, placebo treated group shows lower isometric peak torque (Nm) levels (−2.10% and −2.53%, respectively considering the best or the average of three trials) than the test Formulation of the invention (TPG) treated group during the overall five-day evaluation (comparing before and after downhill exercise). In Table 17, test Formulation of the invention (TPG) group shows lower isometric peak torque (Nm) loss with +37.62%, +50.59% and +60.46% differences for the placebo group (changes from baseline respectively compared directly, 24 h and 48 h after downhill exercise), and a complete recovery with a better level at 72 h than baseline, considering the best of 3 trials. In Table 19, test Formulation of the invention (TPG) group shows significant lower isometric peak torque (Nm) loss with +33.95%, +35.39% and +67.82% differences for the placebo group (changes from baseline respectively compared directly, 24 h and 48 h after downhill exercise), and a complete recovery with a better level at 72 h than baseline, considering the average of 3 trials.

As we can see in Tables 21 and 24, placebo treated group shows lower peak power score (W) levels (−1.2% and −1.13%, respectively considering the best or the average of three trials) than the test Formulation of the invention (TPG) treated group during the overall five-day evaluation (comparing before and after downhill exercise). In Table 22, test Formulation of the invention (TPG) group shows lower peak power score (W) loss with +539.39% difference for the placebo group (changes from baseline compared 24 h after downhill exercise), and a complete recovery with a better level at 48 h than baseline, considering the best of 3 vertical jump trials. In Table 25, test Formulation of the invention (TPG) group shows lower peak power score (W) loss with +414.29% difference for the placebo group (changes from baseline compared 24 h after downhill exercise), and a complete recovery with a better level at 48 h than baseline, considering the average of 3 vertical jump trials.

As we can see in Tables 27 and 30, placebo treated group shows lower height (cm) levels (−1.2% and −1.04%, respectively considering the best or the average of three trials) than the test Formulation of the invention (TPG) treated group during the overall five-day evaluation (comparing before and after downhill exercise). In Table 28, test Formulation of the invention (TPG) group shows lower height (cm) loss with +2625% and 1085.71% differences for the placebo group (changes from baseline respectively compared 24 h and 48 h after downhill exercise), considering the best of 3 vertical jump trials. In Table 31, test Formulation of the invention (TPG) group shows lower height (cm) loss with +184.21% and 680% differences for the placebo group (changes from baseline respectively compared 24 h and 48 h after downhill exercise), considering the average of 3 vertical jump trials.

As we can see in Tables 33 and 36, placebo treated group shows lower velocity (m/s) levels (−0.8% and −2.03%, respectively considering the best or the average of three trials) than the test Formulation of the invention (TPG) treated group during the overall five-day evaluation (comparing before and after downhill exercise). In Table 34, test Formulation of the invention (TPG) group shows lower velocity (m/s) loss with +157.89% and 975% differences for the placebo group (changes from baseline respectively compared 24 h and 48 h after downhill exercise), considering the best of 3 vertical jump trials. In Table 37, test Formulation of the invention (TPG) group shows lower velocity (m/s) loss with +182.35% and 720% differences for the placebo group (changes from baseline respectively compared 24 h and 48 h after downhill exercise), and a complete recovery with a better level at 72 h than baseline, considering the average of 3 vertical jump trials.

As we can see in Table 38, placebo treated group shows lower range of motion (degrees) level (0.76%) than the test Formulation of the invention (TPG) treated group during the overall five-day evaluation (comparing before and after downhill exercise). In Table 39, test Formulation of the invention (TPG) group shows complete recovery with a better level of range of motion (degrees) than placebo at 72 h than baseline during knee flexion.

Altogether, this shows that test Formulation of the invention (TPG) supplementation can help relieving, treating, decreasing and/or preventing muscle soreness in a subject during and/or after exercise and can be used in the treatment muscle pain and/or muscle fatigue. It also shows that test Formulation of the invention (TPG) supplementation can help improving and/or maintaining functional performance, muscle recovery, muscle function, muscle power and muscle strength in a subject during and/or after exercise.

As demonstrated in the examples herein, the treatment with the test formulation (TPG) results in an improvement in muscle recovery through pain (VAS scale), damage biomarker (circulating levels of Creatine kinase), isometric and isokinetic function (torque, power, and work capacity in quadriceps), peak power (vertical jump height, velocity, and power), range of motion (knee flexion), perceived wellness and wellbeing (psychometric test), and perceived exertion during exercise (rating scale). Supplementation with the test Formulation show better improvement over Placebo in males and females independently and together. This is the first time that a curcuminoid containing formulation shows an effect on functional performance (such as muscle strength power, muscle recovery) and on the reduction of muscle soreness in female subjects.

This demonstrates that test Formulation of the invention (TPG) has an effect on functional performance (such as muscle strength power, muscle recovery) and on reducing muscle soreness after exercise and that this effect is reached using much lower doses of curcuminoids when compared with standard curcumin supplements formulations.

The invention claimed is:

1. A composition comprising i) curcuminoids; ii) from about 30% to about 85% by weight of the composition of acacia gum; iii) about 0.5% to about 5% by weight of the composition of one or more saponins; and iv) a pharmaceutically acceptable carrier for use in improving and/or maintaining muscle strength and/or isometric and isokinetic function in a subject and/or relieving, treating, and/or decreasing muscle soreness in a healthy subject during and/or after exercise, wherein the composition provides curcuminoids in an amount of from about 50 mg/dose to about 300 mg/dose.

2. A medicament comprising a composition comprising i) curcuminoids; ii) from about 30% to about 85% by weight of the composition of acacia gum; iii) about 0.5% to about 5% by weight of the composition of one or more saponin(s); and iv) a pharmaceutically acceptable carrier for the treatment of muscle pain and/or muscle fatigue in a subject after exercise by oral administration.

3. A composition comprising i) curcuminoids; ii) from about 30% to about 85% by weight of the composition of acacia gum; iii) about 0.5% to about 5% by weight of the composition of one or more saponins; and iv) a pharmaceutically acceptable carrier for use in reducing muscle damage by decreasing the levels of creatine kinase (CK) in a subject during and/or after exercise or in preventing the muscle damage by preventing the increase of the levels of creatine kinase (CK) in a subject during and/or after exercise, wherein the composition provides curcuminoids in an amount of from about 50 mg/dose to about 300 mg/dose.

4. A method for improving and/or maintaining muscle strength and/or isometric and isokinetic in a subject, and/or relieving, treating, and/or decreasing muscle soreness in a healthy subject during and/or after exercise comprising the administration of an effective amount of a composition comprising i) curcuminoids; ii) from about 30% to about 85% by weight of the composition of acacia gum; and iii) about 0.5% to about 5% by weight of the composition of one or more saponins to a subject in need thereof, wherein the composition provides curcuminoids in an amount of from about 50 mg/dose to about 300 mg/dose.

5. The method according to claim 4, wherein improving and/or maintaining functional performance is due to improving and/or maintaining muscle recovery, improving and/or maintaining muscle function, improving and/or maintaining muscle power, improving and/or maintaining muscle strength and/or improving and/or maintaining perceived wellness and wellbeing.

6. The method according to claim 5, wherein muscle function is isometric and isokinetic function.

7. The method to claim 4, wherein muscle soreness is delayed onset muscle soreness and/or acute muscle soreness.

8. The method according to claim 4, wherein the curcuminoids are selected from the group consisting of curcumin and its phase I or phase II metabolites, demethoxycurcumin and its phase I or phase II metabolites, bisdemethoxycurcumin and its phase I or phase II metabolites and mixtures thereof.

9. The method according to claim 8, wherein curcuminoids are selected from the group consisting of curcumin, demethoxycurcumin (DMC), bisdemethoxycurcumin (BDMC) and mixtures thereof.

10. The method of claim 4, wherein the composition comprises an amount of curcuminoids from about 30 mg to about 1500 mg.

11. The method of claim 4, wherein the curcuminoids are provided by extraction and optionally purification from the root of turmeric, oleoresin turmeric root, defatted oleoresin turmeric root and mixtures thereof.

12. The method according to claim 4, wherein the acacia gum is present in the composition in an amount from about 50% to about 60% by weight of the composition.

13. The method of claim 4, wherein the one or more saponin(s) is selected from the group consisting of quillaja saponin(s), *yucca* saponins, tea saponins, peanut saponins, spinach saponins, sugar beet saponins, yam saponins, blackberry saponins, liquorice root saponins, primula root saponins, ginseng saponins and mixtures thereof.

14. The method of claim 4, wherein the at least one saponin(s) is present in the composition in an amount from about 0.5% to about 3% by weight of the composition.

15. The method of claim 4, wherein the composition comprises particles having an average diameter of from about 100 nm to about 10000 nm.

16. The method of claim 4, wherein the composition provides curcuminoids in an amount of from about 50 mg/day to about 1400 mg/day.

17. The method of claim 4, wherein the composition dosage is from about 100 mg to about 300 mg, and the daily dose of curcuminoids is from about 50 mg/day to about 300 mg/day.

18. The method according to claim 4, wherein the composition provides curcuminoids in an amount of about 70 mg/day to about 90 mg/day of curcuminoids, with from about 54 mg/day to about 69 mg/day curcumin and from 16 mg/day to about 21 mg/day of DMC and BDMC.

19. The method according to claim 4, wherein said composition is configured to be administered as a single daily dose.

20. The method according to claim 4, wherein said composition comprises a pharmaceutical, a nutraceutical, or a food composition.

21. The method according to claim 4, wherein the subject is a human.

22. The method according to claim 21, wherein the human is a male or a female.

23. The method according to claim 4, wherein the method provides curcuminoids in a dosage amount selected from the group consisting of about 60 mg/dose, about 70 mg/dose, about 80 mg/dose, about 90 mg/dose, about 100 mg/dose, about 150 mg/dose, about 200 mg/dose and about 300 mg/dose.

* * * * *